United States Patent [19]

Kang et al.

[11]  4,247,639

[45]  Jan. 27, 1981

[54] BACTERIAL POLYSACCHARIDE

[75] Inventors: Kenneth S. Kang, La Jolla; George T. Veeder, III, San Diego, both of Calif.

[73] Assignee: Merck & Co., Inc., Rahway, N.J.

[21] Appl. No.: 74,282

[22] Filed: Sep. 11, 1979

Related U.S. Application Data

[60] Division of Ser. No. 889,163, Mar. 23, 1978, which is a continuation-in-part of Ser. No. 842,646, Oct. 17, 1977, abandoned.

[51] Int. Cl.$^3$ ............................................. C12P 19/04
[52] U.S. Cl. .................................. 435/101; 435/104; 435/253; 435/852
[58] Field of Search ................ 435/101, 104, 253, 852

[56]  References Cited

PUBLICATIONS

Choy et al., Can. Jour. Chem., vol. 51, 1973, pp. 198–207.
Dutton, Chem. Abst., vol. 76, 1972, p. 127306d.

*Primary Examiner*—Lionel M. Shapiro
*Attorney, Agent, or Firm*—Gabriel Lopez; Hesna J. Pfeiffer; Julian S. Levitt

[57]  ABSTRACT

A high-viscosity heteropolysaccharide composed of 33% mannose, 29% glucose, 21% galactose and 17% glucuronic acid, and containing 5.7% acetyl and 4.9% pyruvate.

4 Claims, No Drawings

BACTERIAL POLYSACCHARIDE

RELATED APPLICATION

This is a division of application Ser. No. 889,163 filed Mar. 23, 1978, which is a continuation-in-part of application Ser. No. 842,646, filed Oct. 17, 1977, now abandoned.

BACKGROUND OF THE INVENTION

1. Field of the Invention

The present invention pertains to a novel heteropolysaccharide which is produced by the action of a bacteria on a selected carbon source. Further, the invention pertains to a novel process for producing a heteropolysaccharide by bacterial fermentation of a selected carbon source under controlled conditions.

2. Description of the Prior Art

It is known that heteropolysaccharides can be produced by certain microorganisms. Some of such heteropolysaccharides function as hydrophilic colloids and because of their viscosity properties and rheology have been used as thickening agents for aqueous systems. Illustrative of prior art heteropolysaccharides, their preparation and uses are U.S. Pat. Nos. 3,020,207; 3,256,271; 3,894,976; 3,915,800 and 3,894,976.

As with other fields of technology, research has continued with the objective of discovering new heteropolysaccharides having useful properties as thickening, suspending and/or stabilizing agents.

OBJECTS OF THE INVENTION

It is an object of this invention to provide a new heteropolysaccharide. It is another object to provide a method for making this new compound. A still further object is provision of formulations containing our new heteropolysaccharide as a thickening or suspending or stabilizing agent. These and other objects of the invention will be apparent from the following description of this invention.

SUMMARY OF THE INVENTION

It has now been found that a high viscosity anionic heteropolysaccharide composed of about 33% mannose, 29% glucose, 21% galactose and about 17% glucuronic acid and also containing about 5.7% acetyl and about 4.9% pyruvate is obtained by an aerobic fermentation of an organism isolated from a soil sample from the Canal Zone. This heteropolysaccharide has desirable thickening, suspending and/or stabilizing properties in aqueous systems.

DETAILED DESCRIPTION

The heteropolysaccharide of this invention is a high molecular weight polysaccharide containing primarily carbohydrate residues and a minor amount of protein. It is sometimes referred to as a "gum" but it is believed that the heteropolysaccharide terminology is more accurate and precise. In the following description of our invention it will sometimes be referred to as Heteropolysaccharide S-21.

The bacterium employed in the process of the present invention which is identified as Strain tR-45, is a mutant of *Klebsiella pneumoniae* Strain S-21 that was isolated from the rhizosphere soil of a plant of the genus *Aechmea epiphytes* belonging to the pineapple family. The soil sample was obtained in the Canal Zone. Strain tTR-45 requires thymine for growth at 37° C. but does not require thymine for growth at 30° C. A deposit of Strain tTR-45 was made with the American Type Culture Collection, 12301 Parklawn Drive, Rockville, Maryland 20852, on 11 August 1977 under Accession No. ATCC 31314. The culture is available to the public without restriction.

This organism requires a fermentation medium that supplies a carbon source, a phosphorus source, a nitrogen source, a magnesium source and an iron source. The carbon source typically is hydrolyzed starch with a DE range of 12-31. The starch can be hydrolyzed with commercially available α-amylases. The phosphorus source may be either $Na_2HPO_4$, $NaH_2PO_4$, $K_2HPO_4$ or $KH_2PO_4$ or a mixture thereof. The concentration may range from about 0.025 to about 0.5%. The magnesium source may be supplied with $MgCl_2$ or $MgSO_4$ in concentrations of from about 0.005 to about 0.02%. The nitrogen source may be $NaNO_3$, $KNO_3$, $NH_4NO_3(NH_4)_2SO_4$, or $NH_4Cl$ as well as organic sources such as soy peptone Type T (Sheffield Chemical, Norwich, New York), Promosoy 100 (Central Soya Chemurgy Division), NZ-amine Type A (Sheffield), or Ferm Amine Type IV (Sheffield). The medium may contain either inorganic or organic nitrogen or mixtures thereof. The concentration of inorganic nitrogen in the medium may range from about 0.045 to about 0.2% and with the organic nitrogen from about 0.01 to about 0.1%. The iron may be supplied to the fermentation as $FeCl_3$ or $FeSO_4$ at levels of 1-10 ppm.

The pH of this fermentation preferably is maintained between about 6.3 and about 7.7, and the temperature between about 28° C. and about 33° C. for maximum polysaccharide production.

The fermentation time is typically from about 48 to 60 hours when proper conditions of medium, temperature, pH and other fermentation parameters are met.

DETAILS OF PROCEDURES

The soil sample when received is plated onto yeast-malt (YM) agar, E-1 agar with 1% dextrose and E-1 agar with 1% 42 dextrose equivalent (DE) corn syrup, and an isolate, Strain 21, is picked from a YM agar plate and pure cultured on nutrient agar.

Strain S-21 is plated on minimal medium containing thymine and trimethoprim and incubated at 37° C. for 4 days. Those colonies which grow on the plate are tested for a thymine requirement at 37° C. Those strains that required thymine at 37° C. are tested again for thymine requirement at 30° C. and 37° C. Strain tTR-45 is one of five strains that did not require thymine at 30° C. but did at 37° C. The reversion frequency on minimal medium is about $2 \times 10^{-8}$ revertants/cell.

This mutant can be cultured on blood agar, chocolate agar, brain heart infusion agar, and nutrient agar. These rich media all have sufficient thymine to meet the thymine requirement of tTR-45. This mutant does not grow on minimal medium at 37° C. but will grow on minimal medium with added thymine. The minimum thymine requirement is greater than 5 ppm but less than 10 ppm.

The minimal medium is prepared as follows:

| Salt Solution | |
| --- | --- |
| $K_2HPO_4$ | 10.5 gm. |
| $KH_2PO_4$ | 4.5 gm. |
| $(NH_4)_2SO_4$ | 1.0 gm. |
| Sodium citrate . $2H_2O$. | 0.5 gm. |

| Salt Solution | |
|---|---|
| Water | 470 ml. |

Autoclave the above medium. Then add 1 ml. of a sterile 1 M solution of MgSO$_4$.7H$_2$O, 10 ml. of a 20% sterile glucose solution and when needed, 10 ml. of a sterile 0.5% solution of thymine and 10 ml. of a 0.5% solution of trimethoprim. Add solution to 15 gm. sterile agar in 500 ml. H$_2$O, mix and pour plates.

Urine agar was prepared by diluting sterile urine with an equal volume of agar solution. This did not support the growth of tTR-45 at 37° C.

Tissue medium was prepared in the following manner. Rabbit kidney, lung and liver were removed quickly from a sacrificed animal, cooled in ice, homogenized in an equal volume of water, and autoclaved. After autoclaving, the tissue homogenate was mixed with an equal volume of agar solution and plates poured from this. The total dilution of tissue was 1:4. These media did not support the growth of tTR-45 at 37° C. but did at 30° C. This same media prepared from bovine kidney also did not support the growth of tTR-45 at 37° C. but did at 30° C.

In another experiment in which the liver and lung were not cooled rapidly, and the homogenate allowed to stand at room temperature for about 15 minutes before autoclaving, the media supported the growth of tTR-45 at 37° C. This could have resulted from the liberation of thymidine from the DNA of the organ homogenates by DNases found in the tissues.

Shake flask experiments are done in 500 ml. unbaffled Erlenmeyer flasks. The flasks are incubated on a New Brunswick Model V gyrotary shaker until harvesting. The fermentation temperature is 30° (all temperatures throughout this specification and claims are expressed in degrees Celsius unless indicated otherwise). The product identified as heteropolysaccharide S-21, or more simply S-21, is recovered by precipitation with 2-3 volumes of isopropyl alcohol (IPA), the fibers collected and dried at 55°-65° overnight. One percent reconstituted viscosities are obtained by dissolving two grams of product in 198 grams of deionized water using a Lightnin' mixer. Unless otherwise stated, all viscosities are measured using a Brookfield Model LVF viscometer with the No. 4 spindle at 60 rpm. S-21 gum contains from about 30 to about 37% mannose, from about 26% to about 32% glucose, from about 19% to about 23% galactose and from about 15.3% to about 18.8% glucuronic acid. It has an acetyl content of from about 5.1% to about 6.3%, and a pyruvate content of from about 4.5% to about 5.4%.

The 20 L fermentor scale-ups are done is Fermentation Design fermentors. The fermentations are started at an air rate of 10 L/M and an agitation rate of 200-300 rpm. At 16-24 hours the agitation is increased to 800 rpm. The pH is controlled at 6.6-6.7 with 30% KOH. The fermentation temperature is 30°. The fermentation liquor is pasteurized at 80° for 10 minutes before harvesting.

The taxonomic data on dextrose, lactose, lysine decarboxylase, ornithine decarboxylase, urea and citrate (Simmon's) is obtained using the Enterotube (Roche Diagnostics) system. The malonate, nitrate reduction, esculin hydrolysis, phenylalanine deaminase and Voges-Proskauer are done using the Pathotec (General Diagnostics) test system. Phenylalanine deaminase is also checked in the standard medium for this test according to the method of Harrigan, W. F. and M. E. McCance, Laboratory Methods in Microbiology, Academic Press, 1966, p. 296. Hydrogen sulfide production is tested in Triple Sugar Iron (TSI) agar and also in cysteine broth with lead acetate paper strips, ibid., p. 55. The fermentation of sucrose, fructose, cellobiose, inositol and dulcitol ws checked in Dye's low buffer carbohydrate fermentation medium. Motility is checked on cells from 20-24 hours NA slants by the hanging drop method and by flagellar stains according to the method of Rosen, A. and R. E. Levin, Vibrios from Fish Pen Slime Which Mimic Escherichia coli on Violet Red Bile Agar, Appl. Microbiol., 20:107-112, 1970. Motility is also checked in semi-solid agar.

Alkaline stability is checked by dissolving 2 grams of gum in 160 ml of tap water. Then while mixing, 40 ml of 50% NaOH is added. The viscosity is measured and the samples stored at 43° for seven days. Acid stability is checked by dissolving 4 grams of gum in 147 ml of tap water. Then 53 ml of concentrated HCl are added slowly with good mixing. The viscosity of the samples are measured and the samples stored at 43°. Thermal stability is measured by autoclaving a 1% solution of gum at 15 psi (2 atmospheres) and 121° for 15 minutes followed by rapid cooling. Viscosities are measured before and after heating.

Temperature-viscosity curves are obtained by heating the gum solution in an oil bath or cooling it in an ice bath and then removing the sample from the respective bath and measuring the viscosity. Concentration vs. viscosity curves are obtained by making individual solutions of gum in deionized water and measuring their viscosity.

The effect of pH on the viscosity of a 1% solution is checked by adjusting the pH with HCl or KOH, allowing the sample to set for 15 minutes, then measuring the viscosity. The effect of added electrolyte is checked by adding various concentrations of NaCl to a 1% solution and measuring the viscosity.

Solvent solubilities are obtained by trying to dissolve the gum in various solvents.

The methylene blue compatibility test is carried out by adding 100 ml of a 1% solution of gum to a mixture of one gram of methylene blue in 3.0 ml of glacial acetic acid. The gum is incompatible if it precipitates.

RESULTS:

A. Taxonomy

The taxonomic results are shown in Table 1. The organism is a gram negative, non-motile, non-spore forming rod. It produces acid and gas from glucose, lactose, sucrose, cellobiose and fructose. It produces acid from inositol but does not ferment dulcitol. The organism is positive for the Voges-Proskauer test, lysine decarboxylase, urease, and nitrate reductase. The organism produces enough H$_2$S for a positive test with the lead acetate test procedure, but is negative for H$_2$S on TSI agar which is less sensitive. This organism can use citrate or malonate as the sole carbon source. It does not produce ornithine decarboxylase or phenylalanine deaminase and does not hydrolyze esculin.

On YM agar with organism produces circular, entire, convex colonies which are very mucoid. On nutrient agar the colonies are similar but smaller and less mucoid. No pigment production is observed.

TABLE 1
TAXONOMIC CHARACTERISTICS OF STRAIN tTR-45

| Characteristic | Results |
|---|---|
| Gram Stain | Gram (-) rod |
| Size | $1 \times 2 \mu$ |
| Motility | Non-motile |
| Carbohydrates | |
| Glucose | Acid and Gas |
| Lactose | Acid and Gas |
| Sucrose | Acid and Gas |
| Cellobiose | Acid and Gas |
| Fructose | Acod and Gas |
| Inositol | Acid Acid |
| Dulcitol | No Change |
| Voges-Proskauer | + |
| H₂S Production | |
| Lead Acetate | + |
| TSI | − |
| Lysine Decarboxylase | + |
| Ornithine Decarboxylase | − |
| Phenylalanine deaminase | − |
| Urea | + |
| Citrate | + |
| Malonate | + |
| $NO_3^{31}$ Reduction | + |
| Esculin Hydrolysis | − |

The fact that Strain tTR-45 is a gram negative, non-spore forming rod capable of producing acid and gas from lactose indicates it belongs to the family Enterbacteriaceae. This organism does not produce H₂S on TSI agar, does not produce phenylalanine deaminase, does produce urease and is positive for the Voges-Proskauer test.

B. Fermentation Improvement

The results in Tables 2 and 3 show the medium optimization work done in shake flasks. The results of the first two experiments indicate that E-1 medium is the best, followed by E-1 supplemented with 5 ppm Fe⁺⁺ and in which the NH₄NO₃ is replaced by 0.19% NaNO₃. Calcium carbonate is not an effective substitute for K₂HPO₄. Doubling the NH₄NO₃ concentration has a very deleterious effect on gum production. However, reduction of the NH₄NO₃ concentration by 50% does not drastically effect gum production.

The results with starch hydrolysates indicate that starch with very low dextrose equivalents (DE) can be used in this fermentation. These results indicate a DE range of 13.4 to 31 can be used for this fermentation. Corn syrup (42 DE) give a high yield but results in a product with a much lower viscosity.

The results of two typical 20 L fermentor scale-ups are shown in Table 4. These results indicate that the fermentation should be complete by 52±3 hours with 3% carbon source. The conversion efficiency is about 60%.

TABLE 2
MEDIUM OPTIMIZATION

Seeds are started in YM broth flasks and incubated for 24 hours at 30° on a gyrotory shaker. One percent inoculums are used to inoculate experimental flasks containing medium variations. The carbon source is hydrolyzed starch. The starch DE for experiment I is 21.1 and 17.5 for experiment II. Experiment I is incubated at 30° for 96 hours on a gyrotory shaker while experiment II goes for 72 hours.

| | Medium | Beer Viscosity (cps) | Gum Yield (1%) | 1% Reconstituted Viscosity (cps) |
|---|---|---|---|---|
| I | E-1* | 100,000+ | 1.76 | 3100 |
| | E-1 − NH₄NO₃ +0.19% NaNO₃ | 6,800 | 1.52 | 2450 |
| | E-1 − K₂HPO₄ + 0.5% CaCO₃ | 5,800 | 2.04 | — |
| | E-1 − NH₄NO₃ + 0.19% NaNO₃ + 5 ppm Fe⁺⁺ | 80,000 | 1.64 | 3100 |
| II | E-1 | 100,000+ | 1.98 | 3225 |
| | E-1 + 5 ppm Fe⁺⁺ | 100,000+ | 1.99 | 3200 |
| | E-1 − NH₄NO₃ + 0.19% NaNO₃ + 5 ppm Fe⁺⁺ | 82,500 | 1.94 | 2650 |
| | E-1 − NH₄NO₃ + 0.045% NH₄NO₃ | 67,000 | 1.72 | 2600 |
| | E-1 − NH₄NO₃ + 0.18% NH₄NO₃ | 700 | 1.06 | — |

*E-1 medium is composed of 0.5% K₂HPO₄, 0.09% NH₄NO₃, 0.05% Promosoy 100, and 0.01% MgSO₄ . 7H₂O in tap water.

TABLE 3
CARBON SOURCES FOR STRAIN tTR-45

The inoculum is grown in YM broth for 24 hours at 30° on a gyrotory shaker. A 1% inoculum is used to inoculate flasks containing E-1 medium—NH₄NO₃+0.19% NaNO₃+5 ppm Fe⁺⁺ and the following carbon sources. The starch is hydrolyzed with Tenase (Miles). All staches contain the same enzyme concentration with the DE being varied by altering heating temperatures and times. The flasks are incubated for 72 hours at 30° on a gyrotory shaker.

| Carbon Source | Beer Viscosity (cps) | Gum Yield (%) | % RV (cps) |
|---|---|---|---|
| Corn Syrup 42 DE | 65,000 | 2.09 | 2000 |
| Starch DE 13.4 | 100,000+ | 1.81 | 3600 |
| Starch DE 21.7 | 96,750 | 1.88 | 3250 |
| Starch DE 26.7 | 100,000 | 1.87 | 3150 |
| Starch DE 30.9 | 81,500 | 1.73 | 2850 |

TABLE 4
SCALE-UP OF STRAIN tTR-45 TO 20L FERMENTORS

| EXPERIMENT I | | | | EXPERIMENT II | | | |
|---|---|---|---|---|---|---|---|
| Age (hrs) | Beer Viscosity (cps) | Gum Yield (%) | Residual Carbon Source (%) | Age (hrs) | Beer Viscosity (cps) | Gum Yield (%) | Residual Carbon Source (%) |
| 20 | 130 | — | — | 24 | 1,500 | 1.53 | 0.55 |
| 41 | 6,700 | 1.96 | 0.32 | 48 | 8,200 | 1.90 | 0.15 |
| 65.5 | 93,500 | 1.81 | Complete | 68 | 18,600 | 1.81 | Complete |

1% Product Viscosity -     1% Product Viscosity -

TABLE 4-continued

SCALE-UP OF STRAIN tTR-45 TO 20L FERMENTORS

| | EXPERIMENT I | | | EXPERIMENT II | |
|---|---|---|---|---|---|
| Age (hrs) | Beer Viscosity (cps) | Gum Yield (%) | Residual Carbon Source (%) | Age (hrs) | Beer Viscosity (cps) | Gum Yield (%) | Residual Carbon Source (%) |
| | 3325 cps | | | | 2950 cps | | |

The medium consists of 0.05% K$_2$HPO$_4$, 0.19% NaNO$_3$, 0.01% MgSO$_4$ . 7H$_2$O, 0.05% Promosoy 100 and 3.0% starch. The seed medium is the same with the inoculum rate at 5%. The fermentation temperature is 30°. Agitation and aeration are increased as necessary. The pH is controlled at 6.4–6.6 with 30% KOH. The starch DE is 12 in the first experiment and 19 in the second.

The results indicate that Strain tTR-45 has a good fermentation (conversion efficiency of 50–67%) in an economic medium with a fermentation time of less than 72 hours. The organism will not produce gum from dextrose efficiently, as an excess of acid is produced. However, a wide range of starch hydrolysates (DE 12.9–31) can be used as a carbon source. The use of corn syrup (42 DE) results in a low viscosity product.

The product is easily recovered as fibers by precipitation with 2–3 volumes of isopropyl alcohol.

C. Gum Properties

Also, S-21 has little or no viscosity synergism with locust bean gum. S-21 exhibits no acid or alkaline stability (97–100% viscosity loss). Upon autoclaving at 121° and 15 psi (2 atmospheres) for 15 minutes, it loses 39–46% of its viscosity compared to little or no loss for xanthan gum.

S-21 is soluble in ethylene glycol but insoluble in isopropyl alcohol, ethyl alcohol, methyl alcohol, acetone, and glycerol. It is also incompatible with methylene blue chloride.

The gum is anionic in nature judged by its incompatibility with a cationic dye such as methylene blue.

The gum produced by S-21 is an unusually high viscosity gum. It has a viscosity much higher than that of xanthan gum.

Very little viscosity change is noted in a 1% solution of S-21 gum in the pH range of 4–10. The S-21 gum loses essentially all of its viscosity in acid or alkaline stability tests. It demonstrates, however, an appreciable degree of thermal stability as less than half of its original viscosity is destroyed by autoclaving.

The S-21 gum is very slightly sensitive to the addition of NaCl to a 1% gum solution.

The S-21 gum is somewhat temperature sensitive and loses approximately 17 cps/°C. in a 1% solution. A 0.5% solution is more temperature sensitive than a 1.0% solution.

At low concentration levels such as 0.1%, S-21 gum has a much higher viscosity than xanthan gum in deionized water and similar viscosities in tap or brine water. At equivalent concentrations of from about 0.4% to about 1.4%, S-21 has a higher viscosity than xanthan gum.

TABLE 5

VISCOSITIES AT 0.1% CONCENTRATION

The viscosity is measured on a Brookfield Model LVF viscometer using the UL adapter.

| | S-21 | Xanthan Gum |
|---|---|---|
| Deionized H$_2$O | 51.5 cps | 29 cps |
| Tap H$_2$O | 21 cps | 23 cps |
| Brine H$_2$O | 8 cps | 5.5 cps |

The results in Table 5 show a comparison of 0.1% viscosities in deionized water, tap water and brine water for S-21 and xanthan gum. The results are similar except that the deionized water viscosity for S-21 is much higher than that of xanthan gum.

TABLE 6

RHEOLOGICAL DATA

| | RHEOLOGICAL DATA | | |
|---|---|---|---|
| | S-21 | S-10 | S-7 |
| Thixotropy | 1.06 | 1.08 | 1.06 |
| Yield Point | 27.2 | 6.6 | 33 |
| Low pseudoplhasticity | 142 | 80 | 160 |
| High pseudoplhasticity | 388 | 172 | 459 |

The data in Table 6 represent a comparison of rheological data for S-21, S-10 (described in U.S. Pat. No. 3,933,788) and S-7 (described in U.S. Pat. No. 3,960,832). The thixotropy is about the same for all three gums. The yield point for S-21 very close to that of S-7. The pseudoplasticity values for S-21 are closer to S-7 than to those of S-10.

D. Gum Component Analysis

Five mg of S-21 gum are added to 2 ml of 1N H$_2$SO$_4$; the tube is sealed and heated to 100° in a boiling water bath for 8 hours. The tube is opened and the solution neutralized with BaCO$_3$. The barium sulfate is removed by filtration and barium ions with H$^+$-charged Amberlite IR 120. The solution is concentrated to a syrup under reduced pressure at 35°. A tentative identification of the sugars present is made by paper chromatography. Alditols are formed by reacting the hydrolysate with sodium borohydride in water overnight. Excess sodium borohydride is removed by treatment with Amberlite IR-120 (H$^+$) and residual boric acid removed as volatile methyl borate by co-distillation several times with methanol. Alditol acetates are formed by reacting with acetic anhydride in pyridine overnight. Water is added to the reaction mixture which is then concentrated to small volume and co-distilled several times with chloroform. The residue is dissolved in chloroform for GLC analysis. GLC is performed with a Hewlett-Packard Model 5750 chromatography using 3% by weight of ECNSS-M on 80/100 Gas Chrom Q at 185°. Sugars are identified by comparison with authentic standards and the proportions of alditol acetates are determined directly from the peak areas on the gas chromatograph by integration.

Uronic Acid Content

The uronic acid content is determined by decarboxylation with 19% hydrochloric acid. Liberated carbon dioxide is trapped in standard sodium hydroxide and determined by back-titration.

Acetyl Content

The acetyl content is determined by deacetylating the gum (0.1% solution) in an oxygen-free atmosphere with a known volume of 0.01 N potassium hydroxide containing 1% (W/V) potassium chloride at room temperature. Aliquots are removed at elapsed time intervals and the acetyl content is determined by back-titration with 0.01 N sulfuric acid using a pH meter.

Pyruvic Acid

The polysaccharide (2 mg/ml) is mixed with an equal volume of 0.2 N-HCl and hydrolysed at 100° for 4 hours.

To a cuvette (1 cm path length) containing 2.4 ml of triethanolamine is added 0.5 ml sample of hydrolysate and 0.1 ml of NADH solution. After mixing, the absorbance is read at 340 nm. Approximately 10 μl (2 units) lactate dehydrogenase is added and the absorbance when constant again determined.

Calculation

Molar extinction coefficient of NADH = 6.22.
Pyruvate content of 0.5 ml sample =

$$\frac{\Delta \text{ absorbance} \times 3 \times 88 \ \mu g}{6.22}$$

The results of the foregoing analyses are as follows:

| | |
|---|---|
| Mannose | 33% |
| Glucose | 29% |
| Galactose | 21% |
| Glucuronic Acid | 17% |
| Acetyl content | 5.7% |
| Pyruvate content | 4.9% |

S-21 gum tends to lump or agglomerate when wet with water. The time required to effect complete solution of the biogum depends on the amount of lumping that occurs initially during preparation of the solutions. It has been found, however, that the dispersibility of S-21 gum is improved by heating the gum in the presence of from about 0.05 weight % to about 5 weight % of a dialdehyde based on the dry weight of S-21 gum. The gum may be treated with the dialdehyde in dry state or in an aqueous medium. The aqueous medium conveniently may be the fermentation beer in which the S-21 gum has been prepared.

The aldehyde may be an aliphatic dialdehyde of from 2 up to about 8 carbon atoms, e.g., glyoxal, malonaldehyde, succinaldehyde, glutaraldehyde, adipinaldehyde or octandialdehyde, or polyglyoxal, an oligomeric form of glyoxalhydrates having from 5 to 10 glyoxalhydrate repeating units. Glyoxal is preferred.

The dialdehyde is added to the beer at about the completion of the fermentation process, preferably with agitation to obtain uniform distribution of the dialdehyde. The beer is then heated to a temperature of from about 70° C. to about 100° C. for a time sufficient to improve the dispersibility of the recovered biogum. In general, this takes at least about 2 minutes, typically from about 2 to about 5 minutes. While longer heating times may be employed, no additional improvement is seen in dispersibility after about 5 minutes of heating.

Heating in the presence of a dialdehyde at a pH below about 7 to obtain improved dispersibility according to the present invention is most conveniently and economically carried out by combining the dialdehyde treatment with pasteurization by heating. In this way no additional time or heating expense is required for the dialdehyde treatment beyond the cost of the dialdehyde itself. While the foregoing description has described the present invention with reference to a fermentation beer, it will be obvious to those skilled in the art that the invention is not limited to fermentation beers but that is is applicable to any aqueous solution of S-21 gum.

The following examples illustrate the present invention without, however, limiting the same thereto.

EXAMPLE 1

Two 500 ml unbaffled shake flasks containing a modified E-1 medium with 3% hydrolyzed starch as the carbon source are inoculated with a one-colony inoculum of Strain tTR-45 from 48 hours YM agar plates. These flasks are incubated at 30° for 24 hours on a New Brunswick Scientific gyrotory shaker Model V at 300 rpm. They are then used to inoculate a 5 L fermentor vessel containing 3 L of the same media. This fermentor has an aeration rate of 1 L/min. with a tip speed of 263 ft/min. At 24 hours this one gallon vessel has a viscosity of 4700 cps and is used to inoculate a 30 L fermentor containing a final volume of 20 L of the same medium. One liter of seed is used as an inoculum. The dextrose equivalent of the hydrolyzed starch is 12. The aeration rate is 10 L/min with a tip speed of 234 ft/min. At 20 hours the viscosity of the fermentation liquor is 130 cps and the tip speed is increased to 470 ft/min. By 41 hours the viscosity of the fermentation liquor has increased to 6700 cps, and the tip speed is increased to 940 ft/min. The fermentation is complete by 65.5 hours with a viscosity of 93,500 cps and a yield of 1.81 gms of product per 100 grams of fermentation liquor. The pH of the fermentation is maintained between 6.6 and 7.7 using 30% KOH and an automatic pH control system. The gum yield, determined by weighing out 100 grams of fermentation liquor followed by the addition of 2–3 volumes of isopropanol and vigorous shaking, is 1.81 g. The resulting fibers are collected by filtration and dried at 105° overnight prior to weighing. The remaining fermentation liquor is treated in the same manner except that the product is dried overnight at 55° prior to milling to a powder. The resulting product has a viscosity of 3325 cps when reconstituted at 1% concentration in deionized water.

EXAMPLE 2

A wall joint cement is formed by adding the following blend:

| | |
|---|---|
| CaCO$_3$ | 383.0 g |
| Mica P-80-F | 75.0 |
| CMC | 2.5 |
| Attagel 40 | 5.0 |
| Bentone LT | 2.5 | slowly to a solution of 4 g of S-21 in 275 g of water using a Hobart Mixer, and then adding 45 g of a latex emulsion.

EXAMPLE 3

A semigloss white latex paint is prepared from the following formulation:

| Material | Pounds | Gallons |
| --- | --- | --- |
| Water | 72.5 | 8.7 |
| Dowicil 75 | 2.0 | 0.17 |
| Tamol 731 25% | 9.0 | 7.00 |
| Propylene Glycol | 60.0 | 1.00 |
| Ethylene Glycol | 22.0 | 2.25 |
| Carbitol Solvent | 18.0 | 2.25 |
| Foamaster G | 2.0 | 0.25 |
| Tipure R-900 | 270.0 | 8.00 |
| Hexylene glycol | 10.0 | 1.31 |
| Aerosol OT 75% (aq) | 2.0 | 0.50 |
| Letdown | | |
| Rhoplex AC 490 | 433.0 | 49.50 |
| Foamaster G | 3.0 | 0.39 |
| 2.5% aqueous solution of S-21 | 178.0 | 20.75 |
| TOTAL | 1080.5 | 102.68 |

The foregoing paint has a unexpected improvement in flow and leveling properties as well as gloss compared to a similar paint formulation viscosified with hydroxyethyl cellulose.

EXAMPLE 4

The pH of a fermentation beer sample (31 liters) prepared as described in Example 1 which contains 1.68 g S-21 per 100 ml of beer is adjusted to 6.3 by addition of concentrated HCl. Glyoxal (40%) is added to a glyoxal level of 3.0% based on weight of gum. After thorough mixing the beer is heated to 80° C., held for 3 minutes at this temperature and then cooled to room temperature. The gum in the pasteruized beer is precipitated by adding 3 volumes of isopropanol, dried in a steam drier at 71° C. and milled. Three grams of the milled gum and 3 grams of a control sample from the same beer treated similarly except omitting the glyoxal treatment are sprinkled evenly over the surface of 297 ml distilled water contained in a 400 ml beaker with a stirrer in place. After 30 seconds the stirrer, which rotates at about 800 rpm, is switched on for one minute. The stirring is then stopped and the solution is screened through a 20-mesh (U.S. Standard) screen, and the wet material remaining on the screen is weighed. The following results are obtained:

| Sample | Weight of Material on Screen (g) |
| --- | --- |
| Glyoxal treated | 0 |
| Control | 22.8 |

What is claimed is:
1. A process for producing Heteropolysaccharide S-21 containing from about 30% to about 37% mannose, from about 26% to about 32% glucose, from about 19% to about 23% galactose and from about 15.3% to about 18.8% glucuronic acid and having an acetyl content of from about 5.1% to about 6.3% and a pyruvate content of from about 4.5% to about 5.4% that comprises growing the organism ATCC 31314 in an aqueous nutrient medium under submerged aerobic conditions and recovering said Heteropolysaccharide S-21.

2. A process according to claim 1 wherein the pH is controlled at from about 6 to about 7.

3. A process according to claim 1 wherein the temperature is controlled at from about 25° C. to about 35° C.

4. A fermentation beer containing from about 1.5% to about 2.1% of heteropolysaccharide S-21.

* * * * *